US00PP15340P2

(12) United States Plant Patent
van den Top

(10) Patent No.: US PP15,340 P2
(45) Date of Patent: Nov. 16, 2004

(54) ***HOSTA* PLANT NAMED 'JUNE FEVER'**

(50) Latin Name: *Hosta tardiana*
Varietal Denomination: June Fever

(76) Inventor: Hendrik Jan van den Top, Wesselseweg 46, 3771 PC Barneveld (NL)

( * ) Notice: Subject to any disclaimer, the term of this patent is extended or adjusted under 35 U.S.C. 154(b) by 0 days.

(21) Appl. No.: 10/770,216

(22) Filed: Feb. 2, 2004

(51) Int. Cl.[7] ..... A01H 5/00
(52) U.S. Cl. ..... Plt./353
(58) Field of Search ..... Plt./353

(56) References Cited

PUBLICATIONS

UPOV ROM GTITM Computer Database GTI Jouve Retrieval Software 2004/02.*
http://www.hostalibrary.com/lemke/pdf/j/june%20fever-%20%20PPAF%2001O%203828%20%20%20.pdf.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of *Hosta* plant named 'June Fever', characterized by its relatively compact plant habit; green and light green variegated leaf color; shiny leaves; and lavender-colored flowers that are positioned above the foliage on strong and erect scapes.

1 Drawing Sheet

Botanical classification/cultivar designation: *Hosta tardiana* cultivar June Fever.

BACKGROUND OF THE INVENTION

The present Invention relates to a new and distinct cultivar of *Hosta* plant, botanically known as *Hosta tardiana*, and hereinafter referred to by the cultivar name June Fever.

The new *Hosta* was discovered by the Inventor in a controlled environment in Barneveld, The Netherlands, as a whole plant mutation of the *Hosta tardiana* cultivar June, not patented, in May, 1998.

Asexual reproduction of the new cultivar by divisions and by tissue-cultured microplants in a controlled environment in Barneveld, The Netherlands since May, 2000, has shown that the unique features of this new *Hosta* are stable and reproduced true to type in successive generations.

SUMMARY OF THE INVENTION

Plants of the cultivar June Fever have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'June Fever'. These characteristics in combination distinguish 'June Fever' as a new and distinct *Hosta* cultivar:

1. Relatively compact plant habit.
2. Green and light green variegated leaf color; leaves shiny.
3. Lavender-colored flowers that are positioned above the foliage on strong and erect scapes.

Plants of the new *Hosta* are most similar to plants of the parent, the cultivar June. In side-by-side comparisons conducted in Barneveld, The Netherlands, plants of the new *Hosta* differed from plants of the cultivar June in the following characteristics:

1. Plants of the new *Hosta* had green and light green variegated leaves whereas plants of the cultivar June had bluish gray-colored leaves.
2. Plants of the new *Hosta* had shinier leaves than plants of the cultivar June.

BRIEF DESCRIPTION OF THE PHOTOGRAPHS

The accompanying colored photographs illustrate the overall appearance of the new *Hosta*, showing the colors as true as it is reasonably possible to obtain in colored reproductions of this type. Colors in the photographs may differ slightly from the color values cited in the detailed botanical description which more accurately describe the actual colors of the new *Hosta*.

The photograph at the top of the sheet comprises a top perspective view of a typical flowering plant of 'June Fever' grown in a container.

The photograph at the bottom of the sheet is a close-up view of typical flowers of 'June Fever'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and the following description were about two years old and grown in 25-cm containers in a glass-covered greenhouse and under conditions which closely approximate commercial production conditions during the spring and summer in Barneveld, The Netherlands. During the production of the plants, day temperatures were about 20° C. and night temperatures were about 16° C.

Botanical classification: *Hosta tardiana* cultivar June Fever.
Parentage: Whole plant mutation of *Hosta tardiana* cultivar June, not patented.

Propagation:

*Propagation method.*—By tissue culture.

*Rooting time.*—Tissue-cultured microplants will initiate roots in about six weeks.

*Root description.*—Fleshy, thin.

Plant description:

*Form.*—Perennial flowering plant; initially upright becoming outwardly arching as leaves develop; inverted triangle, mounded. Moderate to freely clumping. Vigorous growth habit.

*Plant height to top of leaf plane.*—About 30 cm.

*Plant height to top of flowers.*—About 50 cm.

*Plant diameter.*—About 60 cm.

*Foliage description.*—Leaves basal, simple, generally symmetrical, and long-persisting.

*Length: About* 14 to 16 cm. Width: About 7 to 10 cm. Shape: Cordate. Apex: Apiculate. Base: Cordate. Margin: Entire. Texture, upper and lower surfaces: Glabrous; leathery; weakly rugose. Luster, upper and lower surfaces: Dull. Venation: Pinnate, arcuate. Petiole: Length: About 15 to 22 cm. Diameter: About 8 mm. Texture, upper and lower surface: Smooth, glabrous. Color: Developing foliage, upper surface: Center, between 151B and 144B; toward the margins, irregular sectors, 146A. Developing foliage, lower surface: Center, between 151D and 144C; towards the margins, irregular sectors, 146A. Fully developed foliage, upper surface: Center, between 144A and 146B; towards the margins, irregular sectors, 147A, and irregular stripes, 146A. Fully developed foliage, lower surface: Center, 144A; towards the margins, irregular sectors, 146A. Petiole color: Upper surface, 145B; lower surface, 145C; towards the margin, 146C.

Flower description:

*Appearance.*—Single campanulate flowers with fused perianth arranged on racemes. Flowering stems arise from leaf axils. Typically about eight flowering stems per plant; about 15 flowers per raceme. Flowers not persistent. Flowers not fragrant.

*Natural flowering season.*—Summer in The Netherlands; flowering recurrent during this period.

*Flower longevity.*—About seven days.

*Inflorescence height.*—About 9 to 17 cm.

*Inflorescence diameter.*—About 7 to 9 cm.

*Flower length.*—About 4.5 cm.

*Flower diameter.*—About 1.5 cm.

*Flower buds.*—Length: About 1.5 cm. Diameter: About 1 cm. Shape: Ovoid. Color: Close to 91D.

*Perianth.*—Arrangement: Three interior and three exterior tepals; fused. Tepal length: About 4 cm. Tepal width: About 8 mm. Tepal shape: Elongated; apex, apiculate; margin, entire. Tepal texture, upper and lower surfaces: Smooth; glabrous; satiny. Tepal color: When opening, upper and lower surfaces: 85C to 91D. Fully opened, upper and lower surfaces: 85D.

*Floral bracts.*—Arrangement: One per flower at pedical base. Length: About 1 cm. Width: About 5 mm. Shape: Lanceolate. Apex: Acute. Margin: Entire. Color, upper and lower surfaces: Towards the base, 91D to 85B; towards the apex, 146D.

*Pedicel.*—Length: About 5 mm. Diameter: About 2 mm. Aspect: Erect to bent. Strength: Moderately strong. Texture: Smooth, glabrous. Color: Close to 146D.

*Scape.*—Length: About 30 to 45 cm. Diameter: About 1 cm. Aspect: Erect. Strength: Strong. Texture: Smooth; glabrous. Color: 146D.

*Reproductive organs.*—Stamens: Quantity: About five per flower. Stamen length: About 3.5 cm. Stamen color: 4D. Anther length: About 3 cm. Anther color: 103B. Pollen color: 13A. Pistils: Quantity: One per flower. Style length: About 4 cm. Style color: 4D. Stigma color: 6B.

*Seed/fruit description.*—Seed and fruit development have not been observed.

Disease/pest resistance: Plants of the new *Hosta* have not been noted to be resistant to pathogens and pests common to *Hosta*.

Temperature tolerance: Plants of the new *Hosta* have been observed to tolerate temperatures from −30 to 50° C.

It is claimed:

1. A new and distinct cultivar of *Hosta* plant named 'June Fever', as illustrated and described.

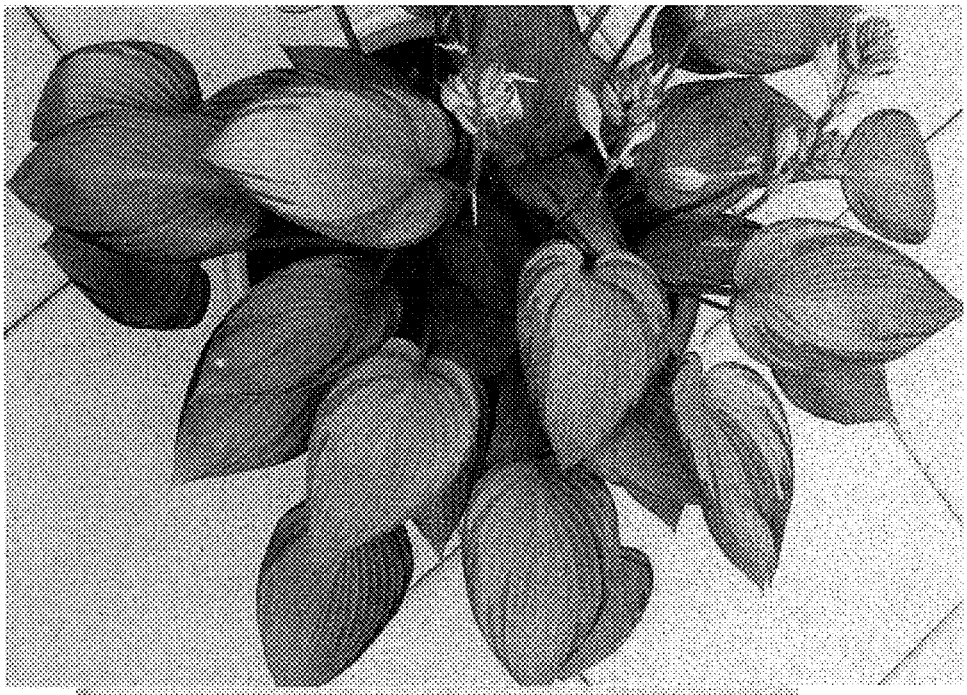
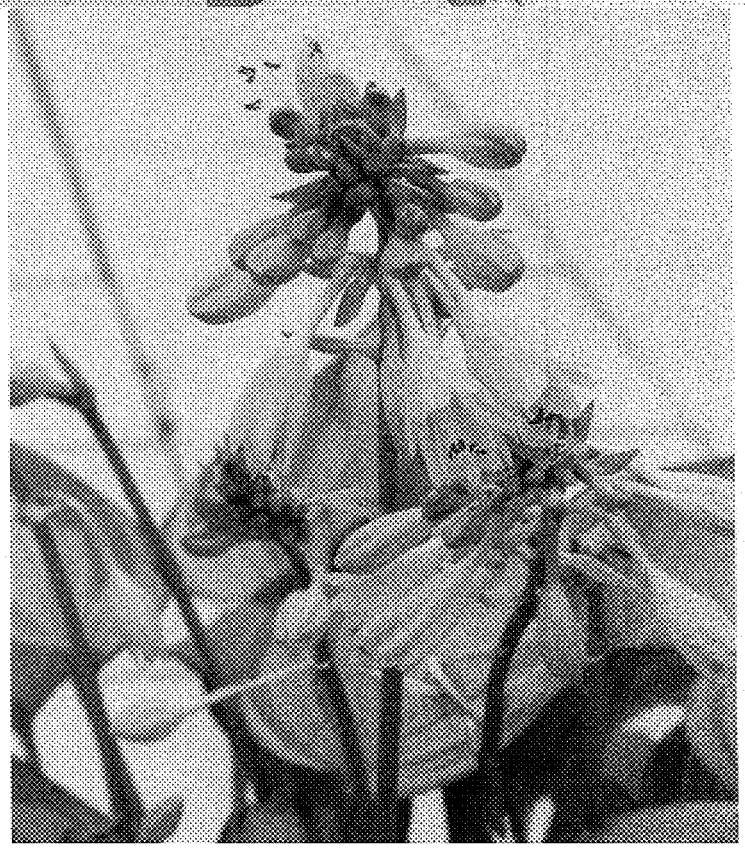

* * * * *